US009089681B2

(12) United States Patent
Ueda et al.

(10) Patent No.: US 9,089,681 B2
(45) Date of Patent: Jul. 28, 2015

(54) MEDICAL STOPCOCK

(71) Applicant: Terumo Kabushiki Kaisha, Shibuya-ku (JP)

(72) Inventors: Yasuhiro Ueda, Tokyo (JP); Takashi Tsukada, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/033,714

(22) Filed: Sep. 23, 2013

(65) Prior Publication Data

US 2014/0018746 A1    Jan. 16, 2014

Related U.S. Application Data

(63) Continuation of application No. PCT/JP2012/057319, filed on Mar. 22, 2012.

(30) Foreign Application Priority Data

Mar. 25, 2011    (JP) .................. 2011-066879

(51) Int. Cl.
*A61M 39/22* (2006.01)
*F16K 11/085* (2006.01)
(Continued)

(52) U.S. Cl.
CPC ............ *A61M 39/22* (2013.01); *A61M 39/223* (2013.01); *A61M 2039/229* (2013.01);
(Continued)

(58) Field of Classification Search
CPC ............. A61M 39/22; A61M 39/223; A61M 2039/229

USPC ............. 137/602, 625.32, 625.4, 625.41, 137/625.46, 861, 862; 251/209; 604/32, 604/99.04, 167.05, 236, 246, 247, 248, 249, 604/250, 256
See application file for complete search history.

(56) References Cited

U.S. PATENT DOCUMENTS

2007/0265581 A1* 11/2007 Funamura et al. ............ 604/248
2007/0287953 A1* 12/2007 Ziv et al. ........................ 604/31
(Continued)

FOREIGN PATENT DOCUMENTS

EP    0 410 898 A2    1/1991
EP    1 790 378 A1    5/2007
(Continued)

OTHER PUBLICATIONS

Extended European Search Report dated Jul. 3, 2014 issued in Application No. 12764012.6.
International Search Report dated May 1, 2012 issued in Application No. PCT/JP2012/057319.

*Primary Examiner* — Rebecca E Eisenberg
*Assistant Examiner* — Anh Bui
(74) *Attorney, Agent, or Firm* — Foley & Lardner LLP (57) ABSTRACT

A medical stopcock includes a main body; and a cock. The main body includes: a tubular portion; an upstream port and a downstream port; and a bypass port provided between the upstream port and the downstream port. The cock includes: a cylindrical portion rotatably accommodated in the tubular portion of the main body; and a handle configured to allow rotation of the cylindrical portion. The cylindrical portion includes: a first flow path groove communicating with the upstream port and the bypass port when the cock is in a reference position, a second flow path groove communicating with the bypass port and the downstream port when the cock is in a reference position, at least one wall portion closing openings of the upstream port, the bypass port and the downstream port when the cock is rotated by a predetermined amount from the reference position.

6 Claims, 9 Drawing Sheets

(51) Int. Cl.
  *F16K 11/083* (2006.01)
  *F16K 27/06* (2006.01)
(52) U.S. Cl.
  CPC ......... *A61M 2206/20* (2013.01); *F16K 11/085* (2013.01); *F16K 11/0833* (2013.01); *F16K 11/0853* (2013.01); *F16K 27/065* (2013.01)

(56) References Cited

U.S. PATENT DOCUMENTS

| | | | |
|---|---|---|---|
| 2008/0195031 A1* | 8/2008 | Kitani et al. | 604/19 |
| 2008/0199558 A1* | 8/2008 | Abe et al. | 425/568 |
| 2008/0319401 A1 | 12/2008 | Funamura et al. | |

FOREIGN PATENT DOCUMENTS

| | | |
|---|---|---|
| EP | 1 961 443 A1 | 8/2008 |
| JP | S-50-033326 U | 4/1975 |
| JP | 2003-159336 A | 6/2003 |
| JP | 2003159336 A * | 6/2003 |
| JP | 2007-143830 A | 6/2007 |
| JP | 2008-511371 A | 4/2008 |
| JP | 2008-188371 A | 8/2008 |
| JP | 2009-183583 A | 8/2009 |
| WO | WO-2004/101061 A1 | 11/2004 |
| WO | WO-2006/025054 A2 | 3/2006 |
| WO | WO-2013/146752 A1 | 10/2013 |

\* cited by examiner

MEDICAL STOPCOCK

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/057319 filed on Mar. 22, 2012, which is based upon and claims the benefit of priority of Japanese Application No. 2011-066879 filed on Mar. 25, 2011, the entire contents of which are hereby incorporated by reference in their entireties.

BACKGROUND

The present disclosure relates to a medical stopcock which is used when injecting a medical fluid into a patient.

In the medical field, a medical stopcock such as a three-way stopcock is often used in an infusion set or the like. For example, if a three-way stopcock is used, a different type of medical fluid can be easily mixed and injected in the course of injecting a predetermined medical fluid into a patient with the infusion set.

In addition, as the medical stopcock, a structure into which bacteria does not enter is desirable. A medical stopcock is disclosed in Japanese Patent Publication No. JP-A-2003-159336, which can prevent bacteria from invading from a bypass port by blocking the inside of a branch pipe from an external atmosphere by a partition wall.

However, in the medical stopcock disclosed in JP-A-2003-159336, there is a problem in that the medical fluid is retained in a bypass port. In addition, there are various types of the medical fluids which are injected from the bypass port. For example, a case is conceivable in which a medical fluid for raising blood pressure is injected from the bypass port and, after several hours, a medical fluid for dropping blood pressure is injected. Even though only a small amount of the medical fluid for raising blood pressure remains in the inside of the bypass port after the medical fluid for raising blood pressure is injected from the bypass port, inconvenience may be caused when the medical fluid for raising blood pressure which remains therein is pushed out by the medical fluid for dropping blood pressure which is injected after several hours. Therefore, it is preferable that an amount of the medical fluid retained in the inside of the medical stopcock is reduced to as little as possible.

Furthermore, in a three-way stopcock of the related art, since the flow of the medical fluid can be generally stopped in some or the whole of a flow path by rotating a cock by approximately 45 degrees, it is not preferable that such operability is lowered.

Embodiments of the present invention are provided in view of such problems and an object of certain embodiments of the invention is to provide a medical stopcock which reduces retention of a medical fluid in the inside thereof more than the related art and maintains operability similar to the related art.

SUMMARY

A medical stopcock comprises a main body; and a cock. The main body includes: a tubular portion; an upstream port and a downstream port provided on an outer circumference of the tubular portion; and a bypass port provided between the upstream port and the downstream port. The cock includes: a cylindrical portion rotatably accommodated in the tubular portion of the main body; and a handle configured to allow rotation of the cylindrical portion. The cylindrical portion includes: a first flow path groove on an outer circumferential surface of the cylindrical portion, the first flow path groove communicating with the upstream port and the bypass port when the cock is in a reference position, a second flow path groove on an outer circumferential surface of the cylindrical portion, the second flow path groove communicating with the bypass port and the downstream port when the cock is in a reference position, and at least one wall portion closing openings of the upstream port, the bypass port and the downstream port when the cock is rotated by a predetermined amount from the reference position. The first flow path groove and the second flow path groove are formed by bypassing the at least one wall portion. The upstream port, the bypass port and the downstream port communicate with each other when the cock is in the reference position.

BRIEF DESCRIPTION OF DRAWINGS

FIG. 1 illustrates a configuration of a medical stopcock according to one embodiment, FIG. 1A being a perspective view of a main body, FIG. 1B being a perspective view of a two-flow path type cock and FIG. 1C being a development view of a groove portion of the cock.

FIG. 2 illustrates flow of a medical fluid flowing from an upstream port to a downstream port via a bypass port in a case where all three ports are opened using the two-flow path type cock, FIG. 2A being an explanatory view of a first half of the flow, FIG. 2B being an explanatory view of a second half of the flow, and FIG. 2C being a cross-sectional view taken along line A-A in FIG. 2B.

FIG. 3 illustrates a case where only the bypass port and the downstream port are opened using the two-flow path type cock, FIG. 3A being an explanatory view of a case where the medical fluid from the upstream port does not flow through the inside of the medical stopcock, FIG. 3B being an explanatory view of the flow of the medical fluid flowing from the bypass port into which the medical fluid is injected to the downstream port and FIG. 3C being a cross-sectional view taken along line B-B in FIG. 3B.

FIG. 4 illustrates a case where the flow of the medical fluid is stopped by rotating the cock by approximately 45 degrees using the two-flow path type cock, FIG. 4A being an explanatory view of a state of an upstream port side, FIG. 4B being an explanatory view of a state of a downstream port side, and FIG. 4C being a cross-sectional view taken along line C-C in FIG. 4B.

FIG. 5 illustrates a one-flow path type cock according to one embodiment, FIG. 5A being a perspective view of the one-flow path type cock, and FIG. 5B being a development view of the groove portion of the cock.

FIG. 6 illustrates a flow of the medical fluid flowing from the upstream port to the downstream port via the bypass port in a case where all three ports are opened using the one-flow path type cock, FIG. 6A being an explanatory view of a first half of the flow, FIG. 6B being an explanatory view of a second half of the flow, and FIG. 6C being a cross-sectional view taken along line D-D in FIG. 6B.

FIG. 7 illustrates a case where only the bypass port and the downstream port are opened using the one-flow path type cock, FIG. 7A being an explanatory view of a case where the medical fluid from the upstream port does not flow through the inside of the medical stopcock, FIG. 7B being an explanatory view of the flow of the medical fluid flowing from the bypass port into which the medical fluid is injected to the downstream port, and FIG. 7C being a cross-sectional view taken along line E-E in FIG. 7B.

FIG. 8 illustrates a case where the flow of the medical fluid is stopped by rotating the cock by approximately 45 degrees using the one-flow path type cock, FIG. 8A being an explanatory view of a state of the upstream port side, FIG. 8B being an explanatory view of a state of the downstream port side, and FIG. 8C being a cross-sectional view taken along line F-F in FIG. 8B.

DETAILED DESCRIPTION

Embodiments of the invention provide a medical stopcock including: a main body; and a cock, in which the main body includes a tubular portion; an upstream port and a downstream port provided on an outer circumference of the tubular portion; and a bypass port provided between the upstream port and the downstream port, in which the cock includes a cylindrical portion rotatably accommodated in the tubular portion of the main body; and a handle for operating the cylindrical portion to be rotated, in which the cylindrical portion includes a first flow path groove communicating with the upstream port and the bypass port, and a second flow path groove communicating with the bypass port and the downstream port on an outer circumferential surface thereof in a state in which the cock is in a reference position; and in which the cylindrical portion includes a wall portion closing openings of the upstream port, the bypass port and the downstream port when the cock is rotated by a predetermined amount from the reference position, in which the first flow path groove and the second flow path groove are formed by bypassing the wall portion, and in which the upstream port, the bypass port and the downstream port communicate with each other in a state in which the cock is in the reference position.

In addition, in some embodiments of the invention, it is preferable that the first flow path groove include a groove corresponding to the upstream port communicating with the upstream port, a first groove corresponding to a bypass port communicating with the bypass port, a first circumferential groove communicating with the groove corresponding to the upstream port and the first groove communicating with the bypass port, and the second flow path groove include a groove corresponding to the downstream port communicating with the downstream port, a second groove corresponding to a bypass port communicating with the bypass port, and a second circumferential groove communicating with the second groove corresponding to the bypass port and the groove corresponding to the downstream port.

In addition, in some embodiments of the invention, for example, the first circumferential groove may bypass the first wall portion to one end side and the other end side of the cylindrical portion, and the second circumferential groove may bypass the second wall portion to one end side and the other end side of the cylindrical portion.

In addition, in some embodiments of the invention, for example, the first circumferential groove may bypass the first wall portion to one end side of the cylindrical portion, and the second circumferential groove may bypass the second wall portion to the other end side of the cylindrical portion.

As described above, when the cock is in the reference position, the medical fluid flowing from the upstream port to the downstream port also passes through the inside of the bypass port so that retention of the medical fluid in the inside of the medical stopcock (in particular, in the inside of the bypass port) can be reduced more than the related art by providing each groove described above in the outer circumferential surface of the cylindrical portion of the cock.

In addition, in some embodiments of the invention, it is preferable that a first rib be provided between the first groove corresponding to the bypass port and the second groove corresponding to the bypass port of the cylindrical portion of the cock to lead a medical fluid from the upstream port into the bypass port side of the main body.

Therefore, the medical fluid from the upstream port is further led to the bypass port side by the first rib and the retention of the medical fluid in the inside of the bypass port can be further reduced.

In addition, in some embodiments of the invention, it is preferable that a second rib be provided inside the bypass port of the main body to be positioned on an extension of the first rib when the cock is in the reference position and to further lead the medical fluid from the upstream port into the bypass port side.

Therefore, the medical fluid from the upstream port is further led to the bypass port side by the second rib which is positioned in the extension of the first rib and the retention of the medical fluid in the inside of the bypass port can be further reduced.

In addition, in some embodiments of the invention, it is preferable that the wall portion include a first wall portion positioned between the groove corresponding to the upstream port and the first groove corresponding to the bypass port, a second wall portion positioned between the second groove corresponding to the bypass port and the groove corresponding to the downstream port, and a third wall portion positioned between the groove corresponding to the downstream port and the groove corresponding to the upstream port.

Therefore, since the medical fluid can be stopped in some or the whole of a flow path by three wall portions when the cock is rotated slightly, it is possible to maintain operability similar to the related art.

According to embodiments of invention, it is possible to provide the medical stopcock which eliminates the retention of the medical fluid in the inside thereof and maintains operability similar to the related art.

Hereinafter, a form (hereinafter, referred to as an embodiment) for carrying out embodiments of the invention will be described with reference to drawings (also appropriately referring to drawings other than mentioned drawings). Furthermore, in one embodiment, a medical fluid also includes a form of fluid as a whole even though containing solids such as colloidal particles in addition to a complete form of fluid.

Figure 1A:
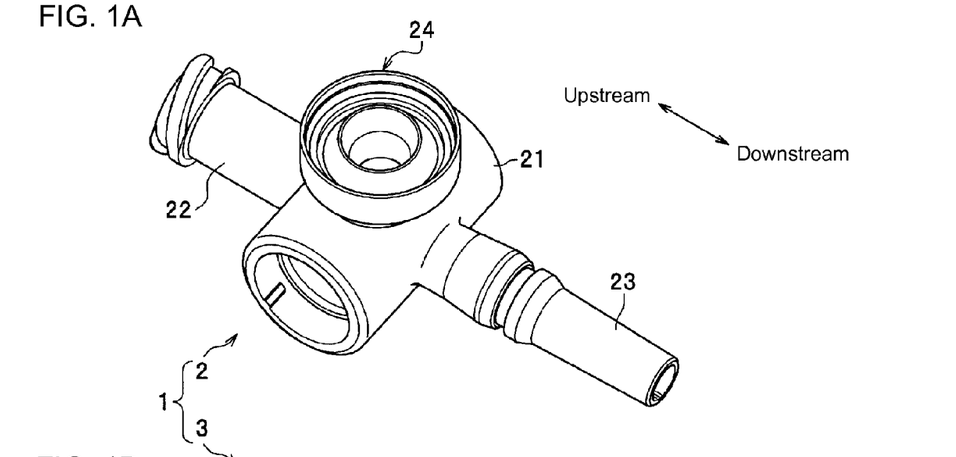
Figure 1B:
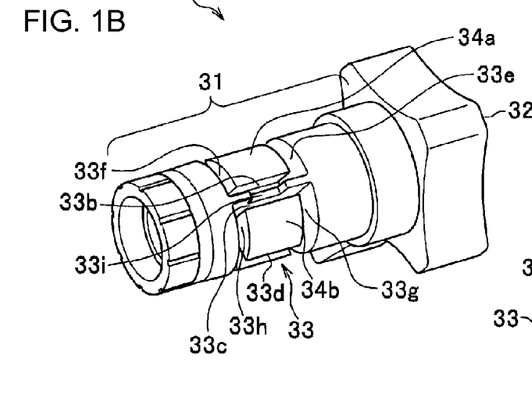

As illustrated in FIGS. 1A and 1B, a medical stopcock 1 of the embodiment includes a main body 2 and a cock 3. Furthermore, for example, a material of the main body 2 or the cock 3 may be a synthetic resin such as polycarbonate, polypropylene, polyacrylamide, and polyethylene terephthalate; however, the material is not limited to these. Furthermore, as the cock 3, a two-flow path type (details are described below) will be described first and then a one-flow path type (details are described below) will be described.

As illustrated in FIG. 1A, the main body 2 includes an upstream port 22 and a downstream port 23 having a flow path for continuously conducting flow of a medical fluid in the inside thereof, a tubular portion 21 which is disposed between the upstream port 22 and the downstream port 23, and rotatably accommodates a cylindrical portion 31 (described below) of the cock 3 in the inside thereof, and a bypass port 24 which is provided in the tubular portion 21 and has a flow path receiving a medical fluid other than the medical fluid flowing through the upstream port 22 and the downstream port 23 in the inside thereof. Furthermore, when using the medical stopcock 1, the bypass port 24 of the main body 2 is not in an opened state but, for example, a cap 25 holding a valve 27 with a cap auxiliary member 25a is mounted (see FIGS. 2A and 2C).

Figure 1C:
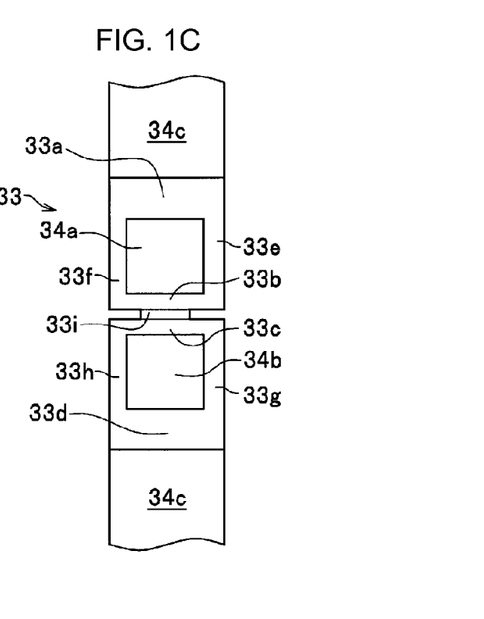

As illustrated in FIGS. 1B and 1C, the cock 3 includes a handle 32 which is operated by a user to be rotated, the cylindrical portion 31 which is rotatably accommodated in the tubular portion 21 of the main body 2, and a groove portion 33 which is provided along an outer circumferential surface of the cylindrical portion 31.

The groove portion 33 is includes a longitudinal groove 33a (a first flow path groove and a groove corresponding to the upstream port), a longitudinal groove 33b (a first flow path groove and a first groove corresponding to the bypass port), a longitudinal groove 33c (a second flow path groove and a second groove corresponding to the bypass port), a longitudinal groove 33d (a second flow path groove and a groove corresponding to the downstream port), a circumferential groove 33e (a first flow path groove and a first circumferential groove), a circumferential groove 33f (a first flow path groove and a first circumferential groove), a circumferential groove 33g (a second flow path groove and a second circumferential groove), a circumferential groove 33h (a second flow path groove and a second circumferential groove), and a central groove 33i (a first flow path groove, a second flow path groove, a first groove corresponding to the bypass port, and a second groove corresponding to the bypass port), and has substantially a shape of "8" as a whole.

In other words, the circumferential grooves 33e and 33f are disposed by bypassing both sides (one end side and the other end side) of the cylindrical portion 31 in an axial direction so that an outer circumferential surface between the longitudinal groove 33a and the longitudinal groove 33b forms a wall portion 34a (a first wall portion) having a size and a position by which at least the upstream port 22 can be closed.

Similarly, the circumferential grooves 33g and 33h are disposed by bypassing both sides (one end side and the other end side) of the cylindrical portion 31 in the axial direction so that an outer circumferential surface between the longitudinal groove 33c and the longitudinal groove 33d forms a wall portion 34b (a second wall portion) having a size and a position by which at least the downstream port 23 can be closed.

Therefore, as long as the wall portion 34a and the wall portion 34b satisfying the condition described above can be formed, each groove may not be linear and some or the whole thereof may be curved. In addition, in the outer circumferential surface of the cylindrical portion 31, a wall portion 34c (a third wall portion) is formed in a semicircular portion in which the groove portion 33 is not present.

In addition, in the embodiment, a cross-sectional area of a flow path end 221 (see FIG. 2A) of the upstream port 22 is substantially the same as that of a flow path end 231 (see FIG. 2B) of the downstream port 23. Therefore, the wall portion 34a also can close the downstream port 23 in addition to the upstream port 22 and the wall portion 34b also can close the upstream port 22 in addition to the downstream port 23 by rotating the cock 3.

In addition, the central groove 33i has a rib (a first rib) for further leading the medical fluid from the upstream port 22 to the bypass port 24 side. In addition, the rib may be realized by forming the central groove 33i to be shallow. Hereinafter, "the central groove 33i" refers to a groove which is formed to be shallower than the other grooves.

Next, the flow of the medical fluid flowing through the inside of the medical stopcock 1 will be described. First, a case where three ports (the upstream port 22, the downstream port 23 and the bypass port 24) are opened (the ports communicate with the groove) will be described with reference to FIG. 2. Three ports are opened when the main body 2 and the cock 3 have a positional relationship as illustrated in FIG. 2. At this time, hereinafter, a relative position (a predetermined rotational position) of the cock 3 with respect to the main body 2 is referred to as "a reference position" (the same is also true in FIGS. 5 to 9). In addition, a rotation direction of the cock 3 where a long portion of the cock 3 moves from this position to the upstream port 22 side is referred to as a "counter-clockwise" direction and the rotation direction of the cock 3 where the long portion of the cock 3 moves to the downstream port 23 side is referred to as a "clockwise" direction (the same is also true in FIGS. 5 to 9).

Figures 2A, 2B, 2C:
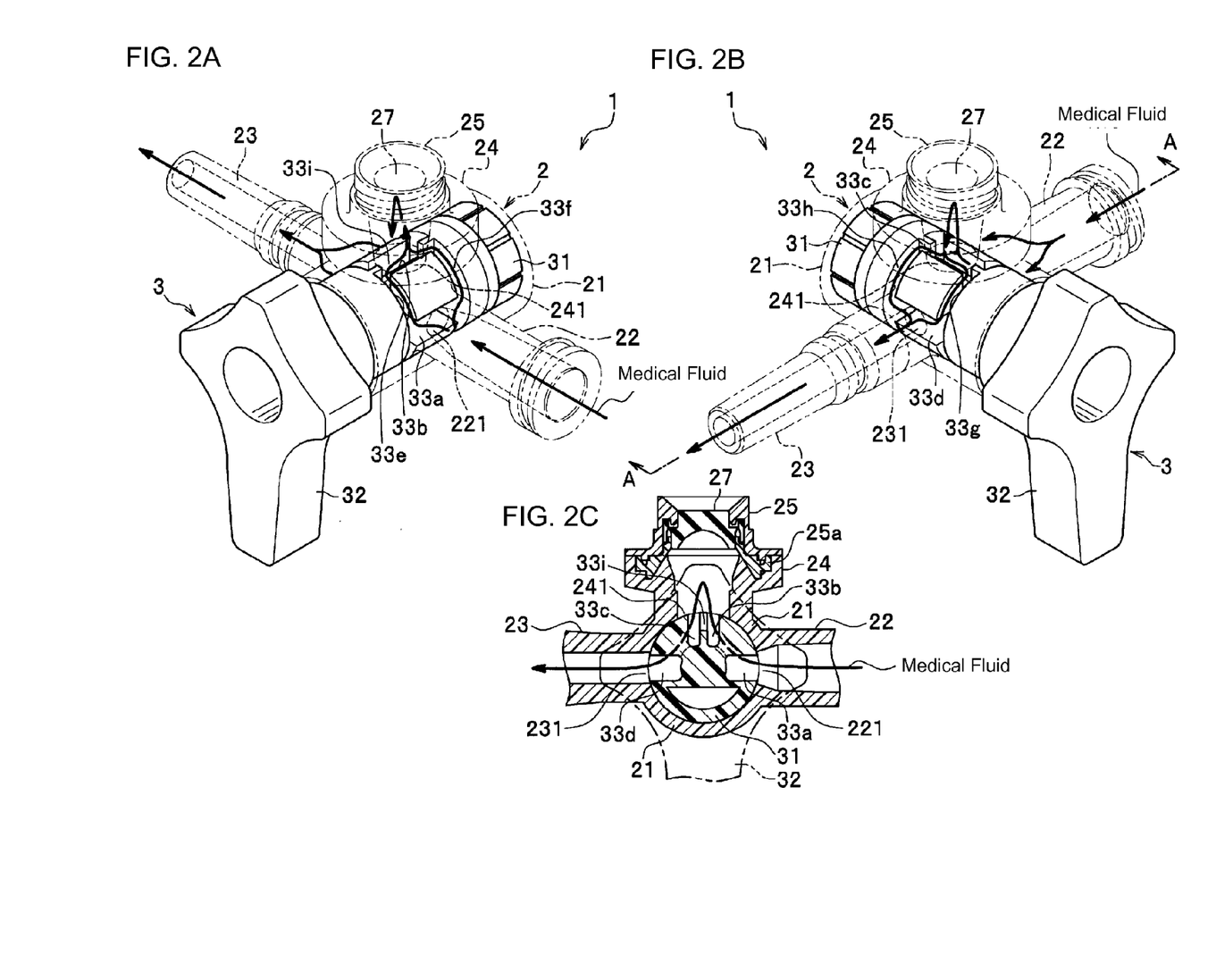

When the cock 3 is in the reference position, as illustrated in FIGS. 2A and 2C, the medical fluid flowing through the upstream port 22 toward the tubular portion 21 enters the longitudinal groove 33a from the flow path end 221, is divided into two left and right flow paths from there, is advanced to the circumferential grooves 33e and 33f, is joined in the longitudinal groove 33b, and enters the bypass port 24 from the central groove 33i.

Subsequently, as illustrated in FIGS. 2B and 2C, the medical fluid enters the longitudinal groove 33c from the bypass port 24, is divided into two left and right flow paths from there, is advanced to the circumferential grooves 33g and 33h, is joined in the longitudinal groove 33d, and enters the downstream port 23 from the flow path end 231.

As described above, the medical fluid flowing from the upstream port 22 to the downstream port 23 also passes through the inside of the bypass port 24 so that retention of the medical fluid in the inside of the medical stopcock 1 (in particular, in the inside of the bypass port 24) can be reduced more than the related art.

In addition, the medical fluid from the upstream port 22 is further led to the bypass port 24 side by the shallow central groove 33i so that the retention of the medical fluid in the inside of the bypass port 24 can be further reduced.

Next, in a case where only the bypass port and the downstream port are opened, the flow of the medical fluid will be described with reference to FIG. 3.

Figures 3A, 3B, 3C:
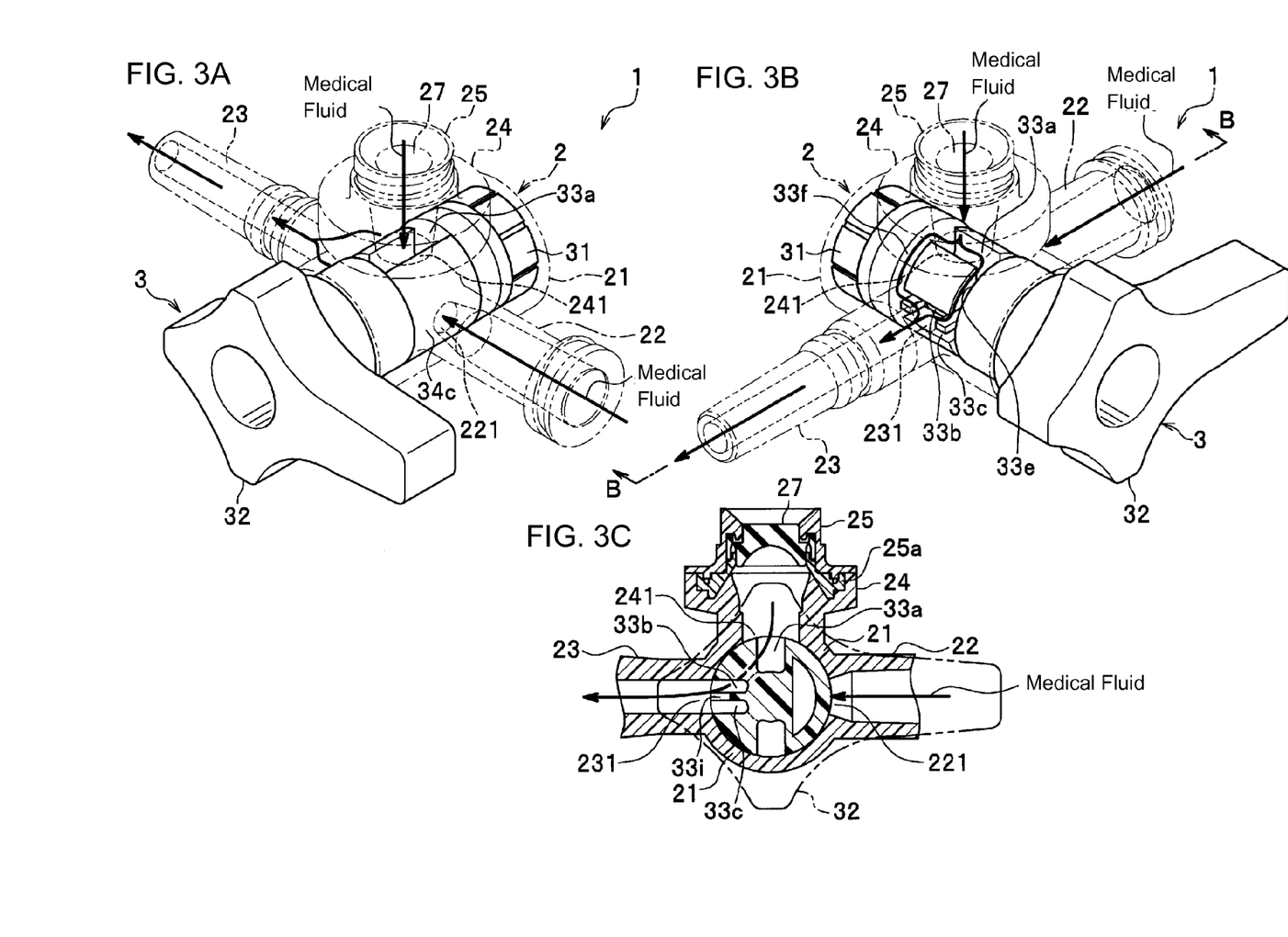

When the cock 3 is rotated by 90 degrees from the reference position in the counter-clockwise direction (a second state), as illustrated in FIGS. 3A and 3C, since the flow path end 221 is closed by the wall portion 34c in the upstream port 22, the medical fluid does not flow. On the other hand, as illustrated in FIGS. 3B and 3C, the medical fluid which enters the inside of the bypass port 24 enters the longitudinal groove 33a, is divided into two left and right flow paths from there, is advanced to the circumferential grooves 33e and 33f, is joined in the longitudinal groove 33b, and enters the downstream port 23 from the flow path end 231.

In addition, when the cock 3 is in a rotation position illustrated in FIG. 3, some medical fluid which enters from the bypass port 24 is retained in the inside of the bypass port 24; however, it is not a problem to be solved by the embodiment. The problem to be solved by the embodiment is that the medical fluid which enters from the bypass port 24 is retained in the inside of the bypass port 24 when the cock 3 is in the rotation position (the reference position) illustrated in FIG. 2 (the same is also true in FIGS. 5 to 9).

Next, a case where the flow of the medical fluid is stopped by rotating the cock 3 by approximately 45 degrees in the clockwise direction will be described with reference to FIG. 4.

Figures 4A, 4B, 4C:
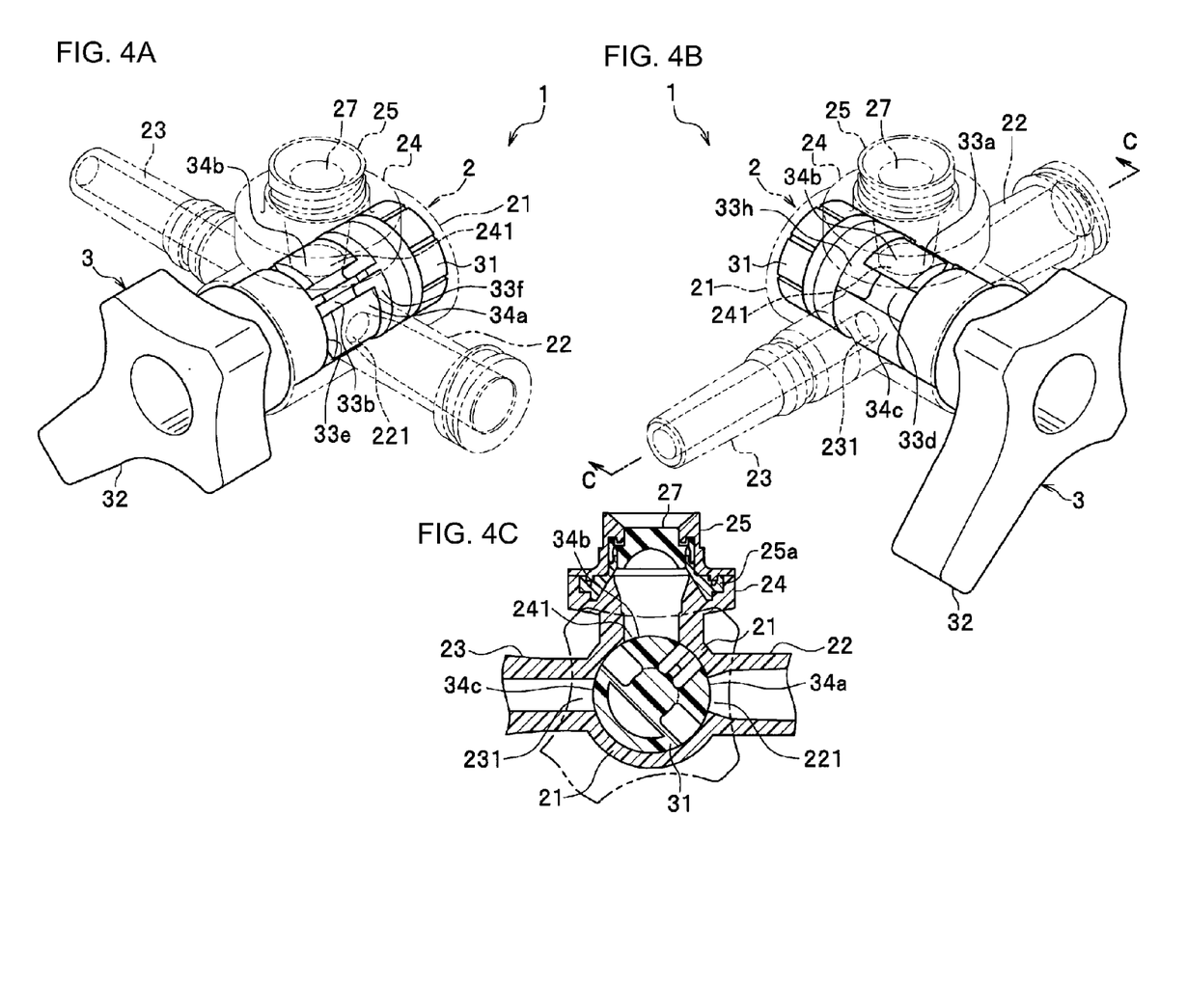

When the cock 3 is rotated approximately by 45 degrees from the reference position in the clockwise direction (a sixth state), as illustrated in FIGS. 4A and 4C, since the flow path end 221 is closed by the wall portion 34a in the upstream port 22, the medical fluid does not flow. In addition, as illustrated in FIGS. 4B and 4C, since the flow path end 231 is closed by the wall portion 34c also in the downstream port 23, the medical fluid does not flow. In addition, as illustrated in FIGS. 4A to 4C, since the flow path end 241 is closed by the wall portion 34b also in the bypass port 24, the medical fluid does not flow. In other words, it is possible to stop the flow of the medical fluid and to maintain operability similar to the related art by providing the groove portion 33, which can form wall portions 34a and 34b on the outer circumferential surface of the cylindrical portion 31 of the cock 3, and only by rotating the cock 3 by approximately 45 degrees.

In addition, when the cock 3 is rotated approximately by 45 degrees from the reference position in the counter-clockwise direction (a first state), similarly, the medical fluid does not flow in the upstream port 22, the downstream port 23 and the bypass port 24.

In addition, when the cock 3 is rotated approximately by 135 degrees from the reference position in the counter-clockwise direction (a third state), the upstream port 22 is closed by the wall portion 34c, the bypass port 24 is closed by the wall portion 34c, and the downstream port 23 is closed by the wall portion 34a.

In addition, when the cock 3 is rotated approximately by 180 degrees from the reference position in the clockwise direction (a fourth state), the upstream port 22 communicates with a groove corresponding to the downstream port 23, the bypass port 24 is closed by the wall portion 34c, and the downstream port 23 communicates with a groove corresponding to the upstream port 22 so that the upstream port 22 communicates with the downstream port 23.

In addition, when the cock 3 is rotated approximately by 135 degrees from the reference position in the counter-clockwise direction (a fifth state), the upstream port 22 is closed by the wall portion 34b, the bypass port 24 is closed by the wall portion 34c, and the downstream port 23 is closed by the wall portion 34c.

Figure 5A:
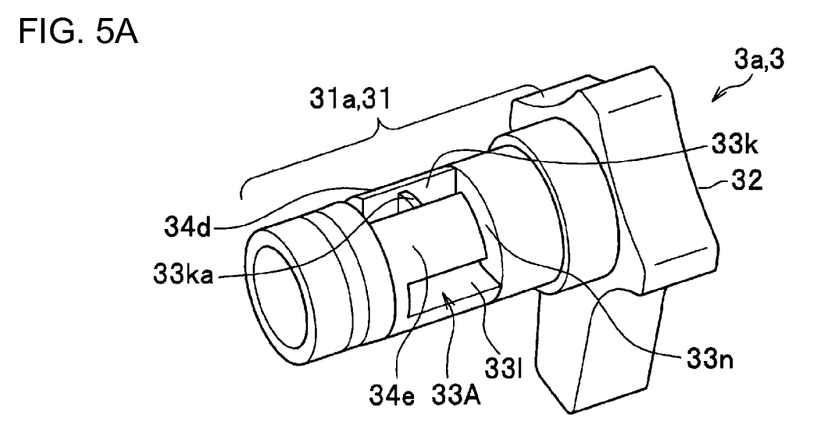
Figure 5B:
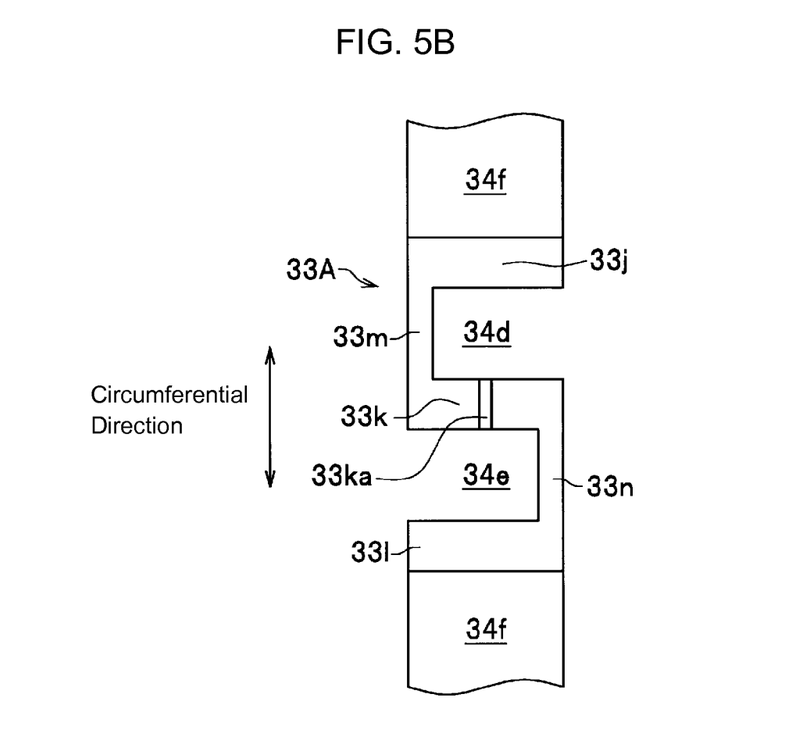

Next, one-flow path type cocks 3a and 3 will be described. As illustrated in FIGS. 5A and 5B, the cock 3 includes the handle 32 which is operated by a user to be rotated, cylindrical portions 31a and 31 which are rotatably accommodated in the tubular portion 21 of the main body 2, and groove portions 33A and 33 which are provided along an outer circumferential surface of the cylindrical portion 31a.

The groove portion 33A includes a longitudinal groove 33j (a first flow path groove and a groove corresponding to the upstream port), a longitudinal groove 33k (a first flow path groove, a second flow path groove, a first groove corresponding to the bypass port (an upstream side higher than a convex portion 33ka), and a second groove corresponding to the bypass port (a downstream side lower than the convex portion 33ka)), a longitudinal groove 33l (a second flow path groove and a groove corresponding to the downstream port), a circumferential groove 33m (a first flow path groove and a first circumferential groove), and a circumferential groove 33n (a second flow path groove and a second circumferential groove), and has substantially a shape of "5" as a whole.

In other words, the circumferential groove 33m is disposed by bypassing one side (one end side) of the cylindrical portion 31a in an axial direction so that an outer circumferential surface between the longitudinal groove 33j and the longitudinal groove 33k forms a wall portion 34d (a first wall portion) having a size and a position by which at least the upstream port 22 can be closed.

Similarly, the circumferential groove 33n is disposed by bypassing one side (the other end side) of the cylindrical portion 31 in the axial direction so that an outer circumferential surface between the longitudinal groove 33k and the longitudinal groove 33l forms a wall portion 34e (a second wall portion) having a size and a position by which at least the downstream port 23 can be closed.

Therefore, as long as the wall portion 34d and the wall portion 34e satisfying the condition described above can be formed, each groove may not be linear and some or the whole thereof may be curved. In addition, in the outer circumferential surface of the cylindrical portion 31a, a wall portion 34f (a third wall portion) is formed in a semicircular portion in which the groove portion 33A is not present.

In addition, similar to a case of the two-flow path type cock 3 (see FIG. 1B), the wall portion 34d also can close the downstream port 23 in addition to the upstream port 22 and the wall portion 34e also can close the upstream port 22 in addition to the downstream port 23 by rotating the cock 3a.

In addition, a central portion of the longitudinal groove 33k has the convex portion 33ka (a first rib) for further leading the medical fluid from the upstream port 22 to the bypass port 24 side. In addition, the rib may be realized by forming the central portion of the longitudinal groove 33k to be shallow.

Next, the flow of the medical fluid flowing through the inside of the medical stopcock 1 (the main body 2 and the cock 3a) will be described. First, a case where three ports (the upstream port 22, the downstream port 23 and the bypass port 24) are opened will be described with reference to FIG. 6.

Figures 6A, 6B, 6C:
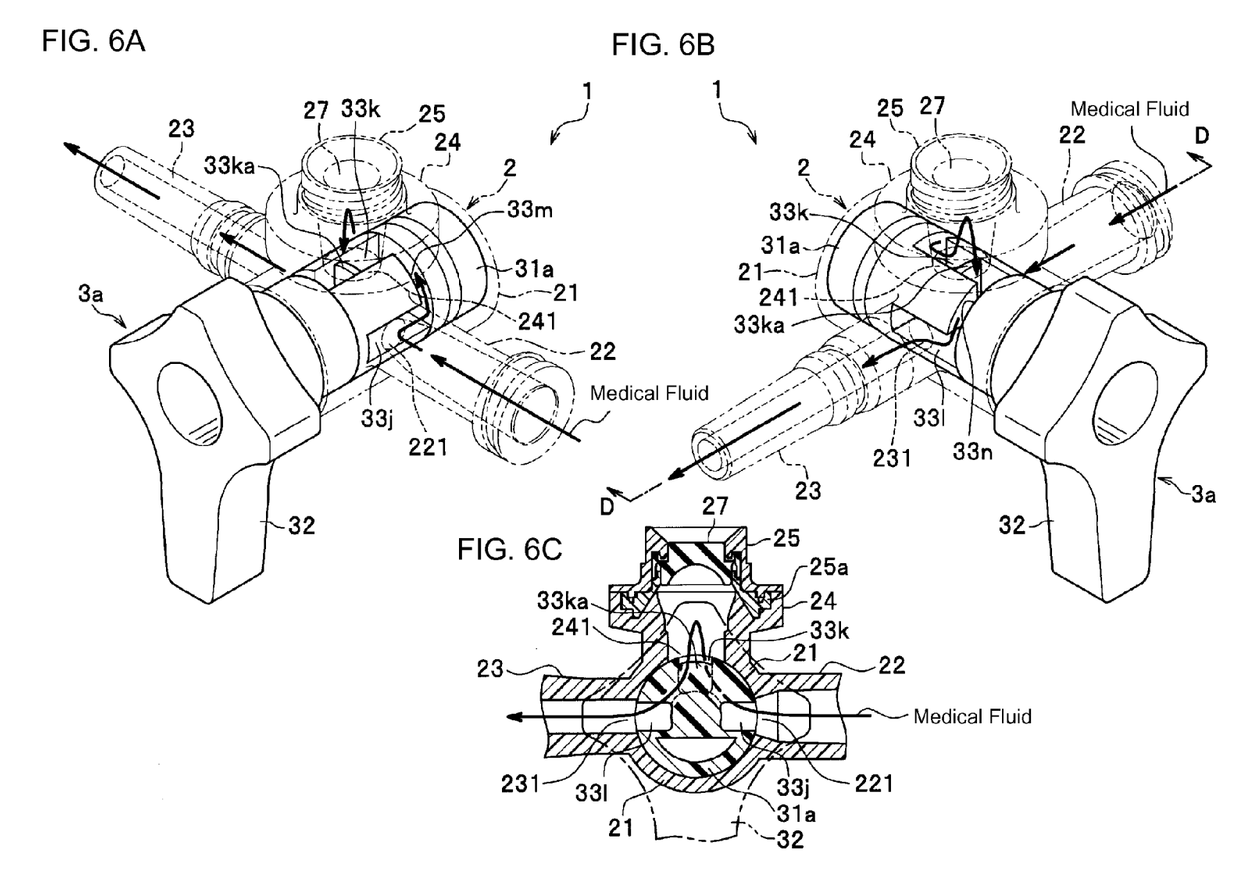

When the cock 3 is in the reference position, as illustrated in FIGS. 6A and 6C, the medical fluid flowing through the upstream port 22 toward the tubular portion 21 enters the longitudinal groove 33j from the flow path end 221, is advanced to the circumferential groove 33m and the longitudinal groove 33k, and enters the bypass port 24 from the front (the front in the flowing direction) of the convex portion 33ka of the longitudinal groove 33k.

Subsequently, as illustrated in FIGS. 6B and 6C, the medical fluid enters the back (the back in the flowing direction) of the convex portion 33ka of the longitudinal groove 33k from the bypass port 24, is advanced to the circumferential grooves 33n and the longitudinal groove 33l, and enters the downstream port 23 from the flow path end 231.

As described above, the medical fluid flowing from the upstream port 22 to the downstream port 23 also passes through the inside of the bypass port 24 so that the retention of the medical fluid in the inside of the medical stopcock 1 (in particular, in the inside of the bypass port 24) can be reduced more than the related art.

In addition, the medical fluid from the upstream port 22 is further led to the bypass port 24 side by the convex portion 33ka so that the retention of the medical fluid in the inside of the bypass port 24 can be further reduced.

Next, in a case where only the bypass port and the downstream port are opened, the flow of the medical fluid will be described with reference to FIG. 7.

Figures 7A, 7B, 7C:
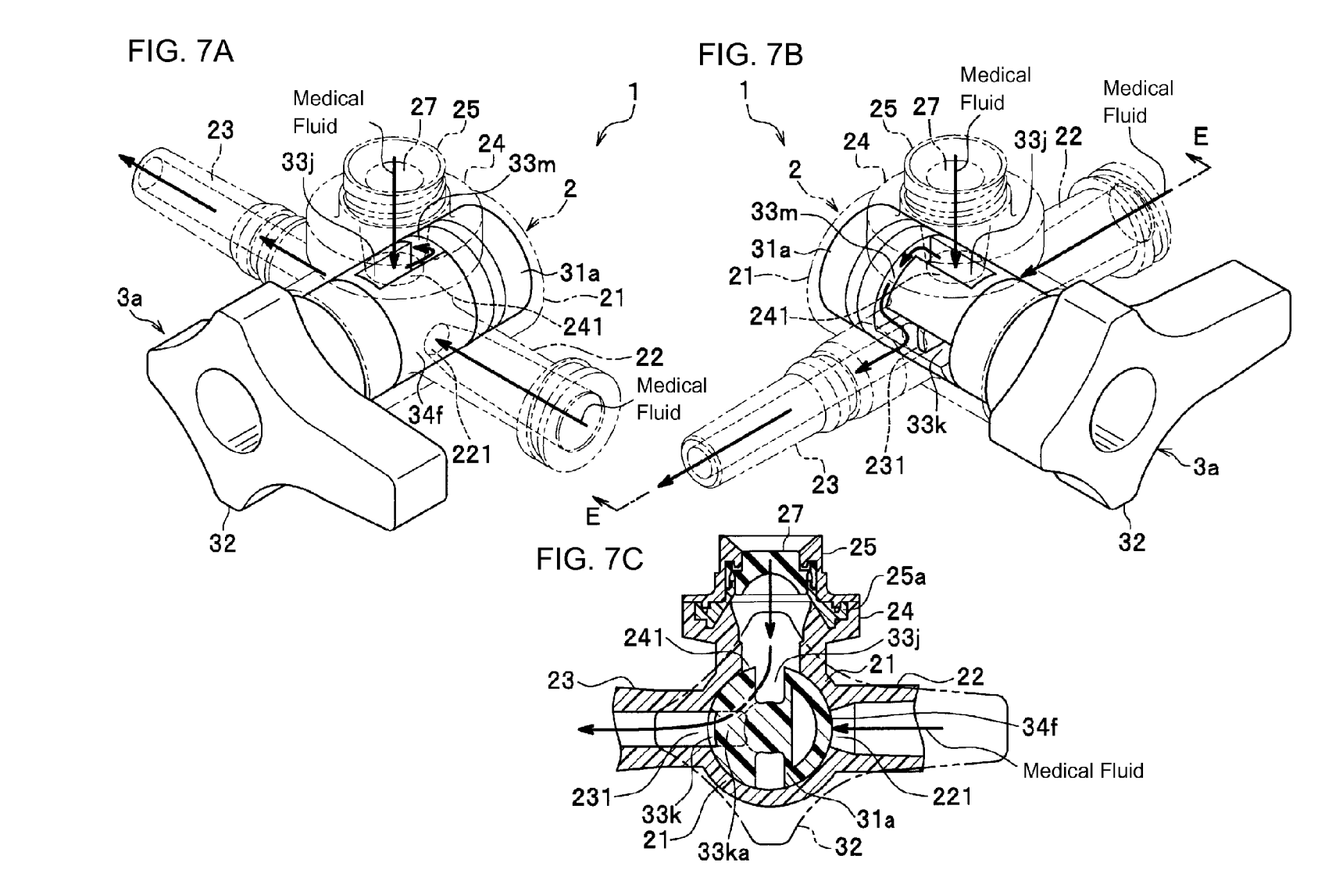

When the cock 3a is rotated by 90 degrees from the reference position in the counter-clockwise direction (the second state), as illustrated in FIGS. 7A and 7C, since the flow path end 221 is closed by the wall portion 34f in the upstream port 22, the medical fluid does not flow. On the other hand, as illustrated in FIGS. 7B and 7C, the medical fluid which enters the inside of the bypass port 24 enters the longitudinal groove 33j, is advanced to the circumferential grooves 33m and the longitudinal groove 33k, and enters the downstream port 23 from the flow path end 231.

Next, a case where the flow of the medical fluid is stopped by rotating the cock 3a by approximately 45 degrees in the clockwise direction will be described with reference to FIG. 8.

Figures 8A, 8B, 8C:
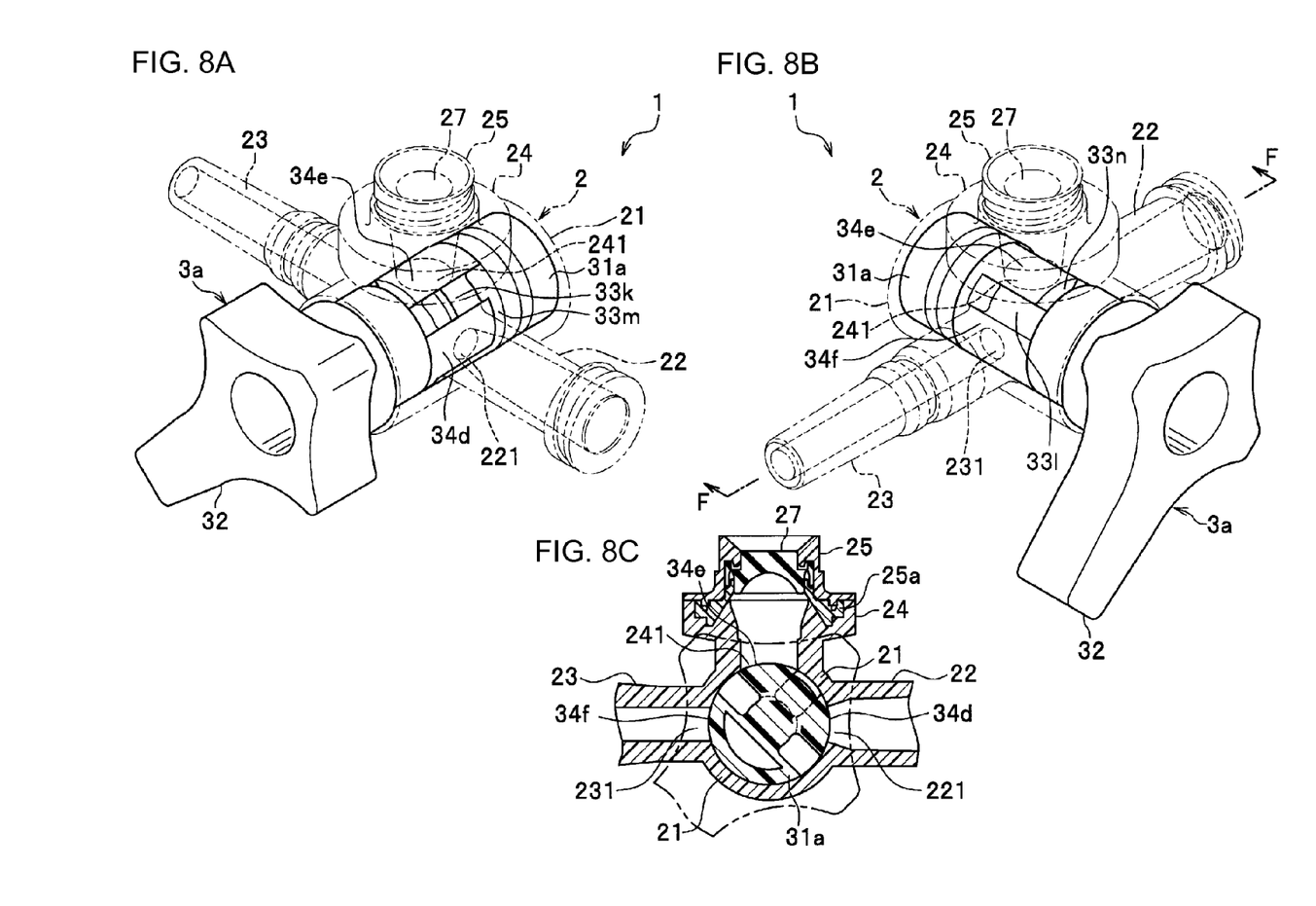

When the cock 3a is rotated approximately by 45 degrees from the reference position in the clockwise direction (the sixth state), as illustrated in FIGS. 8A and 8C, since the flow path end 221 is closed by the wall portion 34d in the upstream port 22, the medical fluid does not flow. In addition, as illustrated in FIGS. 8B and 8C, since the flow path end 231 is closed by the wall portion 34f also in the downstream port 23, the medical fluid does not flow. In addition, as illustrated in FIGS. 8A to 8C, since the flow path end 241 is closed by the wall portion 34e also in the bypass port 24, the medical fluid does not flow. In other words, it is possible to stop the flow of the medical fluid and to maintain operability similar to the related art by providing the groove portion 33A, which can form the wall portions 34d and 34e on the outer circumferential surface of the cylindrical portion 31 of the cock 3, and only by rotating the cock 3a approximately by 45 degrees.

In addition, when the cock 3a is rotated approximately by 45 degrees in the counter-clockwise direction (the first state), similarly, the medical fluid does not flow in the upstream port 22, the downstream port 23 and the bypass port 24.

In addition, since the third state to the fifth state are the same states as the two-flow path type cock 3 (see FIG. 1B), the description thereof will be omitted.

Figure 9A:
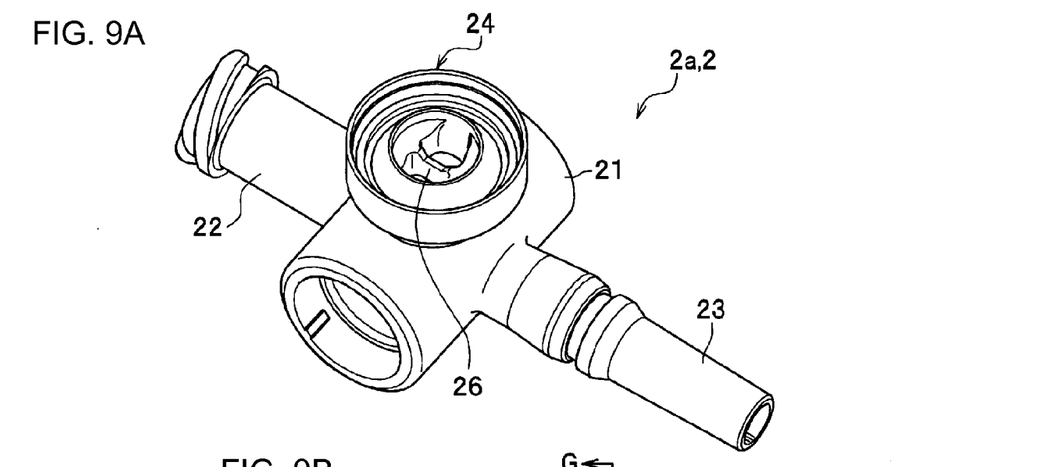
FIG. 9A is a perspective view of a main body in which a rib is provided inside the bypass port as an example of a modification of the main body.
Figures 9B, 9C:
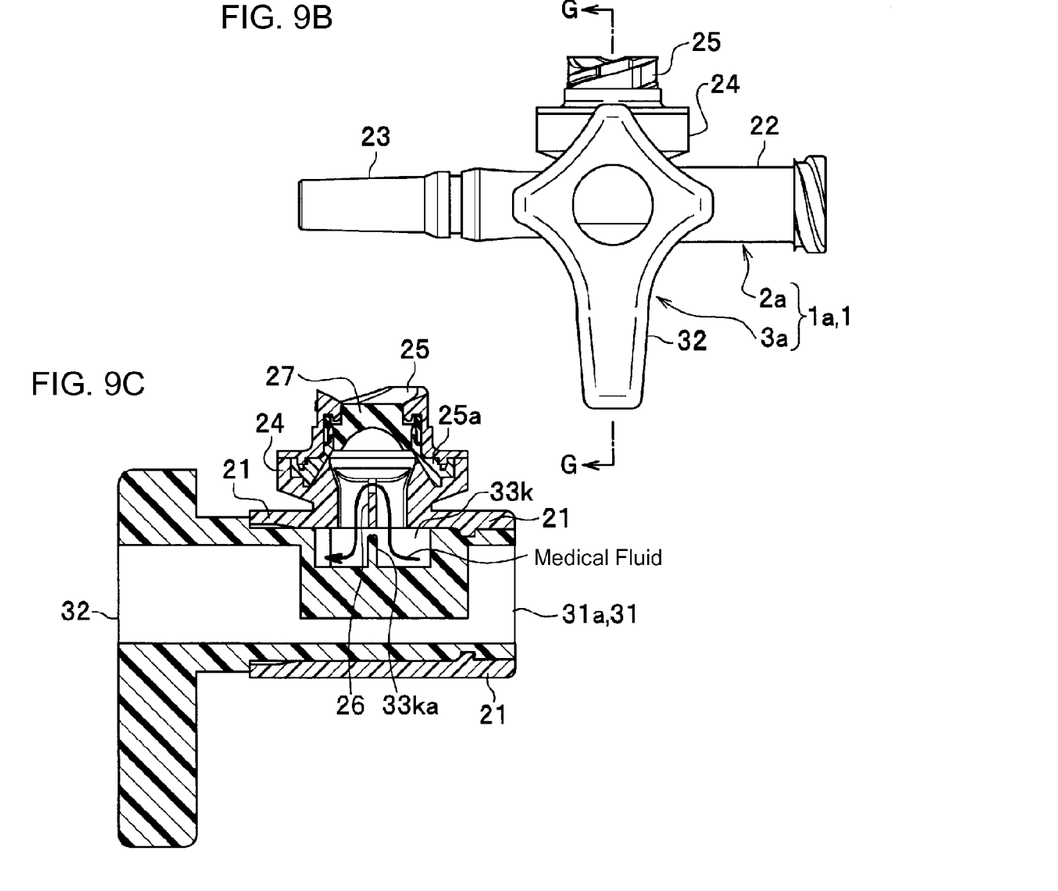
FIG. 9B is a side view of the medical stopcock which is obtained by combining of the main body and the cock illustrated in FIG. 5, viewed from a handle side of the cock.
FIG. 9C is a cross-sectional view taken along line G-G in FIG. 9B.

Next, a modification example of the main body 2 will be described with reference to FIG. 9. As illustrated in FIG. 9A, the main bodies 2a and 2 include a rib 26 (a second rib) (and a peripheral member thereof) in the inside of the bypass port 24 with respect to the main body 2 illustrated in FIG. 1A. The medical stopcock 1a,1 which is obtained by combining the main body 2a and the cock 3a (see FIG. 5) is illustrated in FIG. 9B. As illustrated in FIG. 9C, which is a cross-sectional view taken along line G-G in FIG. 9B, when the medical fluid flows through the longitudinal groove 33k from the right side to the left side, the medical fluid is further led to the bypass port 24 side by the convex portion 33ka, and is further led to the vicinity of the valve 27 which is held by the cap 25 and the cap auxiliary member 25a in the inside of the bypass port 24 by the rib 26 which is positioned in the extension of the convex portion 33ka, and then is returned to the longitudinal groove 33k.

As described above, according to the medical stopcock 1 of certain embodiments, the medical fluid flowing from the upstream port 22 to the downstream port 23 also passes through the inside of the bypass port 24 so that retention of the medical fluid in the inside of the medical stopcock 1 (in particular, in the inside of the bypass port 24) can be reduced more than the related art by providing the groove portion 33 having the above described structure along the outer circumferential surface of the cylindrical portion 31 of the cock 3. In addition, it is possible to stop the flow of the medical fluid and to maintain operability similar to the related art by providing the groove portion 33, which can form the two wall portions 34 ("the wall portions 34a and 34b" or "the wall portions 34d and 34e") described above on the outer circumferential surface of the cylindrical portion 31 of the cock 3, and only by rotating the cock 3 approximately by 45 degrees.

In addition, the medical fluid from the upstream port 22 is further led to the bypass port 24 side by the central groove 33i or the convex portion 33ka so that the retention of the medical fluid in the inside of the bypass port 24 can be further reduced.

In addition, the medical fluid from the upstream port 22 is further led to the bypass port 24 side by the rib 26 which is positioned at the extension of the convex portion 33ka so that the retention of the medical fluid in the inside of the bypass port 24 can be further reduced.

With the above, the description of the embodiments is completed; however, aspects of the invention are not limited to these embodiments.

For example, in the above embodiments, the upstream port 22 and the downstream port 23 form an angle of 180 degrees on the basis of the tubular portion 21; however, they may form other angles such as 90 degrees. In that case, the groove portion 33 corresponding to the degree may be provided on the outer circumferential surface of the cylindrical portion 31 of the cock 3.

In addition, a specific configuration of each portion or each unit may be appropriately modified without departing from the scope of the invention.

What is claimed is:

1. A medical stopcock comprising:
   a main body; and
   a cock,
   wherein the main body includes:
      a tubular portion;
      an upstream port and a downstream port provided on an outer circumference of the tubular portion; and
      a bypass port provided between the upstream port and the downstream port, wherein the cock includes:
      a cylindrical portion rotatably accommodated in the tubular portion of the main body; and
      a handle configured to allow rotation of the cylindrical portion,
      wherein the cylindrical portion includes:
         a first flow path groove on an outer circumferential surface of the cylindrical portion, the first flow path groove communicating with the upstream port and the bypass port when the cock is in a reference position,
         a second flow path groove on an outer circumferential surface of the cylindrical portion, the second flow path groove communicating with the bypass port and the downstream port when the cock is in the reference position, and
         a plurality of wall portions configured to simultaneously close openings of the upstream port, the bypass port and the downstream port when the cock is rotated by a predetermined amount from the reference position,
         wherein the first flow path groove and the second flow path groove are configured to bypass respective ones of the plurality of wall portions,
      wherein the upstream port, the bypass port and the downstream port communicate with each other when the cock is in the reference position,
      wherein the first flow path groove includes:
         a groove corresponding to the upstream port and communicating with the upstream port;
         a first groove corresponding to the bypass port and communicating with the bypass port; and
         a first circumferential groove communicating with the groove corresponding to the upstream port and the first groove corresponding to the bypass port, and
      wherein the second flow path groove includes:
         a groove corresponding to the downstream port and communicating with the downstream port;

a second groove corresponding to the bypass port and communicating with the bypass port; and a second circumferential groove communicating with the second groove corresponding to the bypass port and the groove corresponding to the downstream port.

2. The medical stopcock according to claim 1, wherein a first rib is provided between the first groove corresponding to the bypass port and the second groove corresponding to the bypass port, the first rib being configured to lead a medical fluid from the upstream port into the bypass port side of the main body.

3. The medical stopcock according to claim 2, wherein a second rib is provided inside the bypass port of the main body in proximity to the first rib when the cock is in the reference position, the second rib being configured to further lead the medical fluid from the upstream port into the bypass port side.

4. The medical stopcock according to claim 1, wherein the plurality of wall portions includes:

a first wall portion positioned between the groove corresponding to the upstream port and the first groove corresponding to the bypass port;

a second wall portion positioned between the second groove corresponding to the bypass port and the groove corresponding to the downstream port; and a third wall portion positioned between the groove corresponding to the downstream port and the groove corresponding to the upstream port.

5. The medical stopcock according to claim 4, wherein:

the first circumferential groove has a first path and a second path, wherein the first path of the first circumferential groove bypasses the first wall portion at a first end side of the cylindrical portion, and the second path of the first circumferential groove bypasses the first wall portion at a second end side of the cylindrical portion, and the second circumferential groove has a first path and a second path, wherein the first path of the second circumferential groove bypasses the second wall portion at a first end side of the cylindrical portion, and the second path of the second circumferential groove bypasses the second wall portion at a second end side of the cylindrical portion.

6. The medical stopcock according to claim 4, wherein:

the first circumferential groove bypasses the first wall portion at a first end side of the cylindrical portion, and the second circumferential groove bypasses the second wall portion at an opposing second end side of the cylindrical portion.

* * * * *